US012649896B2

(12) United States Patent
Gleissner et al.

(10) Patent No.: US 12,649,896 B2
(45) Date of Patent: Jun. 9, 2026

(54) DEVICE FOR PROVIDING A CELL SUSPENSION

(71) Applicant: Lonza Cologne GmbH, Cologne (DE)

(72) Inventors: Timo Gleissner, Euskirchen (DE);
Claudiu Todor, Cologne (DE)

(73) Assignee: Lonza Cologne GmbH, Cologne (DE)

( * ) Notice: Subject to any disclaimer, the term of this patent is extended or adjusted under 35 U.S.C. 154(b) by 537 days.

(21) Appl. No.: 18/026,664

(22) PCT Filed: Sep. 21, 2021

(86) PCT No.: PCT/EP2021/075893
§ 371 (c)(1),
(2) Date: Mar. 16, 2023

(87) PCT Pub. No.: WO2022/073754
PCT Pub. Date: Apr. 14, 2022

(65) Prior Publication Data
US 2023/0340386 A1     Oct. 26, 2023

(30) Foreign Application Priority Data
Oct. 6, 2020     (EP) ..................................... 20200202

(51) Int. Cl.
*C12M 1/00*          (2006.01)
(52) U.S. Cl.
CPC ............ *C12M 23/38* (2013.01); *C12M 23/34* (2013.01); *C12M 29/00* (2013.01); *C12M 29/20* (2013.01)
(58) Field of Classification Search
None
See application file for complete search history.

(56) References Cited

U.S. PATENT DOCUMENTS

| 2010/0012665 A1* | 1/2010 | Morrissey ................ B67D 7/78 |
| | | 220/601 |
| 2011/0027877 A1 | 2/2011 | Bertolla |
| 2012/0284991 A1 | 11/2012 | Kusz et al. |
| 2018/0187141 A1 | 7/2018 | Cox, Jr. et al. |
| 2019/0169572 A1 | 6/2019 | Shi et al. |
| 2020/0040294 A1* | 2/2020 | Matsunaga ............ C12M 23/34 |
| 2021/0002600 A1 | 1/2021 | Tsukada et al. |

FOREIGN PATENT DOCUMENTS

| CA | 3094825 A1 | 9/2019 |

OTHER PUBLICATIONS

European Patent Office, Written opinion issued for appl. PCT/EP2021/075893 on Apr. 14, 2022.

* cited by examiner

*Primary Examiner* — Holly Kipouros
(74) *Attorney, Agent, or Firm* — Agris & von Natzmer LLP; Joyce Von Natzmer

(57) ABSTRACT

The invention relates to a device for providing a cell suspension to an apparatus for treating the cells, wherein the device comprises at least one internal space 16 for holding the suspension, and wherein the internal space 16 is at least partially surrounded by a wall 15. The device further comprises at least one inlet port 2 comprising at least one first opening 3 for introducing the suspension into the internal space 16 and at least one outlet port comprising at least one second opening for removing the suspension from said internal space 16. The inlet port 2 further comprises at least one barrier element 6 bordering the first opening 3 at a side furthest to the wall 15 and is partially arranged between the first opening 3 and the internal space 16.

17 Claims, 6 Drawing Sheets b)

a)

b)

a)

DEVICE FOR PROVIDING A CELL SUSPENSION

CROSS-REFERENCE TO RELATED APPLICATIONS

This is the U.S. national stage of international application PCT/EP2021/075893, filed Sep. 21, 2021 designating the United States and claiming priority to European patent application EP 20200202.8, filed Oct. 6, 2020, which is incorporated herein by reference in its entirely.

BACKGROUND OF THE INVENTION

The invention relates to a device for providing a cell suspension to an apparatus for treating the cells, said device comprising at least one internal space for holding the suspension, wherein said internal space is at least partially surrounded by a wall, said device further comprising at least one inlet port comprising at least one first opening for introducing the suspension into said internal space and at least one outlet port comprising at least one second opening for removing the suspension from said internal space.

US 2019/0169572 A1 discloses a system for manufacturing cell therapy products comprising an automated bioreactor and an electroporation unit, wherein a cell culture flows from the bioreactor to the electroporation unit and back again. The system further comprises several disposable consumables such as a cell engineering cassette, an electroporation cartridge, two electroporation reservoirs, and two connection tubing sets. The electroporation reservoirs include inlet and outlet weldable tubing with luer lock connection endings, a cell inlet port within the reservoir housing connected to the external inlet reservoir tubing for sterile cell transfer into the reservoir, a luer lock substrate addition port on the inlet tubing of the reservoir, and a vent filter on the cap for air escape during volume transfer. However, as the cell inlet port of each reservoir is disposed at a central position of the reservoir housing, the cell suspension drops into the internal space of the reservoir from a relatively great height so that each drop collides with the surface of reservoir housing and/or the liquid already present in the reservoir. The cells are therefore highly stressed when they are transferred into the reservoir so that their viability is decreased.

SUMMARY OF THE INVENTION

It is an object of the invention to provide a device for providing a cell suspension to a cell treatment apparatus, which allows for gentle and preserving provision of the cells in order to increase their viability.

The object is achieved by a device as initially mentioned, wherein the inlet port further comprises at least one barrier element bordering the first opening at a side furthest to the wall and being partially arranged between the first opening and the internal space. The barrier element is thus arranged such that the cell suspension introduced into the internal space gently flows along the inner surface of the wall so that dropping of the suspension from the first opening into the internal space and thus collision of suspension drops with any surface can be avoided. When a cell suspension is introduced into the inlet port, the suspension is deflected by the barrier element in direction of the wall so that its flow is decelerated and the suspension flows slowly from the first opening along the wall into the internal space. As a result, the cells are not exposed to mechanical stress so that cell yield can be significantly increased. Moreover, as incalculable cell loss can thus be avoided, reproducibility of test results or product yields is enhanced as well.

In an advantageous embodiment of the invention, the wall comprises at least one recess and the barrier element and the recess form a cavity emptying into the internal space. Thus, the barrier element and the recess are arranged and designed such that the cell suspension introduced into the inlet port is deflected by the barrier element in direction of the recess so that its flow is decelerated. The suspension thus accumulates in the cavity and then flows slowly from the cavity along the wall into the internal space. Accordingly, exposure of the cells to mechanical stress can be further reduced.

In a further advantageous embodiment of the invention, the inlet port is disposed in a region near to the wall and the recess is disposed in a region near to the first opening. Such arrangement ensures that the distance between the first opening and the recess as well as the wall is short so that exposure of the cells to mechanical stress is further reduced. The particular arrangement further allows for easy manufacturing of the device according to the invention.

In another advantageous embodiment of the invention, the inlet port further comprises a tubular channel disposed between the first opening and at least one third opening designed to be connectable to at least one first hose. In a further advantageous embodiment of the invention, the outlet port further comprises a tubular channel disposed between the second opening and at least one fourth opening designed to be connectable to at least one second hose. The device according to the invention can thus be easily connected to containers/reservoirs and/or other devices of a cell treatment/engineering system. For example, the tubular channel(s) of the inlet and/or outlet port can be designed to be a male fitting of a Luer taper connection so as to allow for standardized connection of the device with other parts of a cell treatment/engineering system.

The device according to the invention can thus be used as a reservoir for a cell suspension and optionally a substrate such as DNA, RNA, proteins or other biologically active molecules, said reservoir delivering the cells and optionally the substrate to a cell treatment/engineering system, for example, a large volume cell transfection apparatus.

The inlet port may be part of a cap-like element designed to cover the internal space. The cap-like element can be (reversibly) attached to the wall surrounding the internal space, for example, by means of a snap-action connection. Alternatively or even additionally, the cap-like element can be irreversibly attached to the wall surrounding the internal space, for example, by means of a glued or welded connection. The cap-like element may also be part of the wall, i.e., cap-like element and wall are formed as one part/piece. Moreover, the cap-like element may comprise at least a part of the wall surrounding the internal space of the device according to the invention.

In an advantageous embodiment of the invention, the cap-like element may comprise at least one retainer for holding at least one magnetic element (e.g., a stir bar).

In a further advantageous embodiment of the invention, the transition region (area) between the wall and the outlet port is shaped uniformly. By this measure, the cell suspension can be removed from the internal space completely, almost without any remaining residues. Accordingly, loss of treated cells can be minimized.

The wall and/or the internal space may have any kind of shape/geometry. For example, the wall and/or the internal space may have a spherical, cubic, cylindrical or column-like, or box-shaped or rectangular block form. Preferably, the internal space has an elongated form and a vertical or at least inclined orientation, wherein the inlet port and the outlet port are disposed at opposite ends of the internal space. For example, the device according to the invention may comprise an elongated tube comprising an inlet port at one distal end of the tube and an outlet port at the other distal end of the tube. In a preferred embodiment of the invention, the cell suspension is forced from the inlet port to the bottom of the internal space and/or the outlet port by gravitation.

In an advantageous embodiment of the invention, the outlet port is disposed at a central point at the bottom of the internal space. The outlet port may also be disposed at the deepest point of the internal space, preferably with a steep decline of the bottom. These measures also allow for residue-free removal of the cell suspension so that loss of valuable cells can be minimized.

Basically, the device according to the invention is especially optimized for maximum content retrieval. That is, even a tiny amount of cell suspension such as 1 ml or less can be filled into the device's internal space and still all of it can be removed therefrom. Such complete cell removal cannot be achieved if a conventional reservoir such as a bag is used.

The wall of the device according to the invention may be made of a synthetic material such as Medical Grade Polycarbonate (Makrolon 2458). In a preferred embodiment the synthetic material may be provided with a coating (at least at the inner surface of the wall) and/or inherently modified so as to obtain specific beneficial properties, for example, hydrophobic properties for allowing even smaller amounts of cell suspension (e.g., less than 1 ml) to be completely removed from the internal space of the device.

In a further advantageous embodiment of the invention, the bottom area of the internal space comprises a flat and circular region for receiving and guiding a magnetic element (e.g., stir bar). The cell suspension can thus be thoroughly stirred during the treatment, wherein a smooth and constant movement of the magnetic element is ensured. Accordingly, uneven mixing of the cells and generation of turbulences within the suspension can be avoided so that exposure of the cells to mechanical stress is further reduced.

The device according to the invention may further comprise at least one venting port comprising at least one fifth opening for balancing the pressure within the internal space. The venting port may comprise a venting valve and/or can be provided with a filter element, for example, a sterile membrane filter, in order to avoid contamination of the cell suspension within the internal space.

In a further advantageous embodiment of the invention, at least the outer surface of the wall and/or the cap-like element comprises at least one recess and/or protrusion for fixing a position of the device, preferably if the device according to the invention is hold by a support device as described below.

Furthermore, a support device for holding the device according to the invention is provided, said support device comprising at least one base element and at least one mounting element for holding the device, wherein the mounting element comprises a magnetic means for retaining at least one magnetic element contained in the device. The mounting element serves as a kind of trap for magnetic elements used to stir a cell suspension or a biological/ chemical solution, preferably in the internal space of a device according to the invention. If a device containing a magnetic element is fixed to the support device such that it is guided along the magnetic means, the magnetic element is retained by the magnetic means, fixed at the wall of the device, and thus kept away from the outlet port of the device.

As the magnetic element would otherwise impede removal of the suspension or solution from the device, this feature ensures residue-free removal of the suspension/solution so that loss of valuable material can be further reduced.

The magnetic means may be an integral part of the support device or a separate member that can be (reversibly or irreversibly) mounted on the support device.

The mounting element may further comprise at least one protrusion or recess for fixing the device, wherein the protrusion and/or recess of the mounting element corresponds to a recess and/or protrusion of the device's wall and/or cap-like element, respectively. Thus, the device can be fixed easily and securely to the support device in a particular position that is useful for a specific application.

"Cell suspension" as used herein refers to a fluid comprising a liquid (e.g., water, saline solution, cell culture medium, or the like), in which cells are suspended. The cells may be higher eukaryotic cells such as human or animal cells, microorganisms such as bacteria or yeast, or biologically active organelles or vesicles. The liquid may further include a substrate (e.g., DNA, mRNA, proteins or other biologically active molecules) that is mixed with the suspended cells.

The invention is further exemplarily described in detail with reference to the figures.

DESCRIPTION OF EXEMPLARY AND PREFERRED EMBODIMENTS OF THE INVENTION

Figure 1:
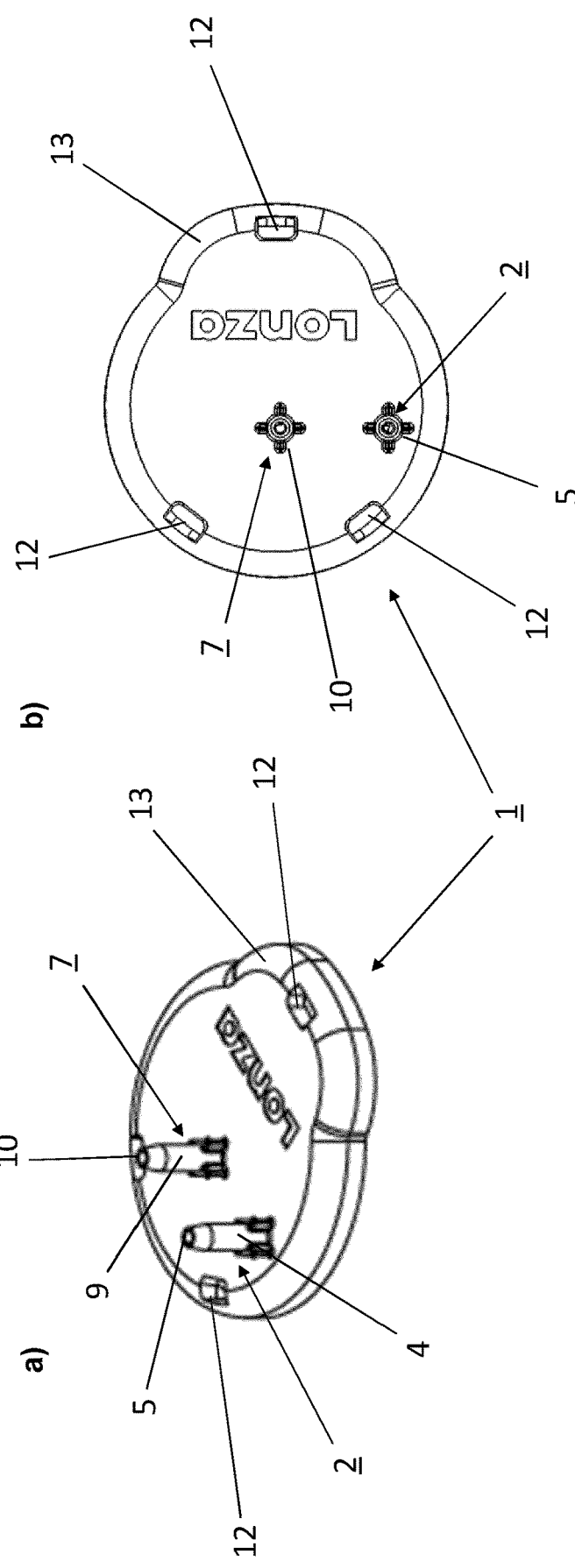
FIG. 1 shows schematic representations of a preferred embodiment of a part (cap) of a device according to the invention.
a) Perspective view
b) Top view
Figure 2:
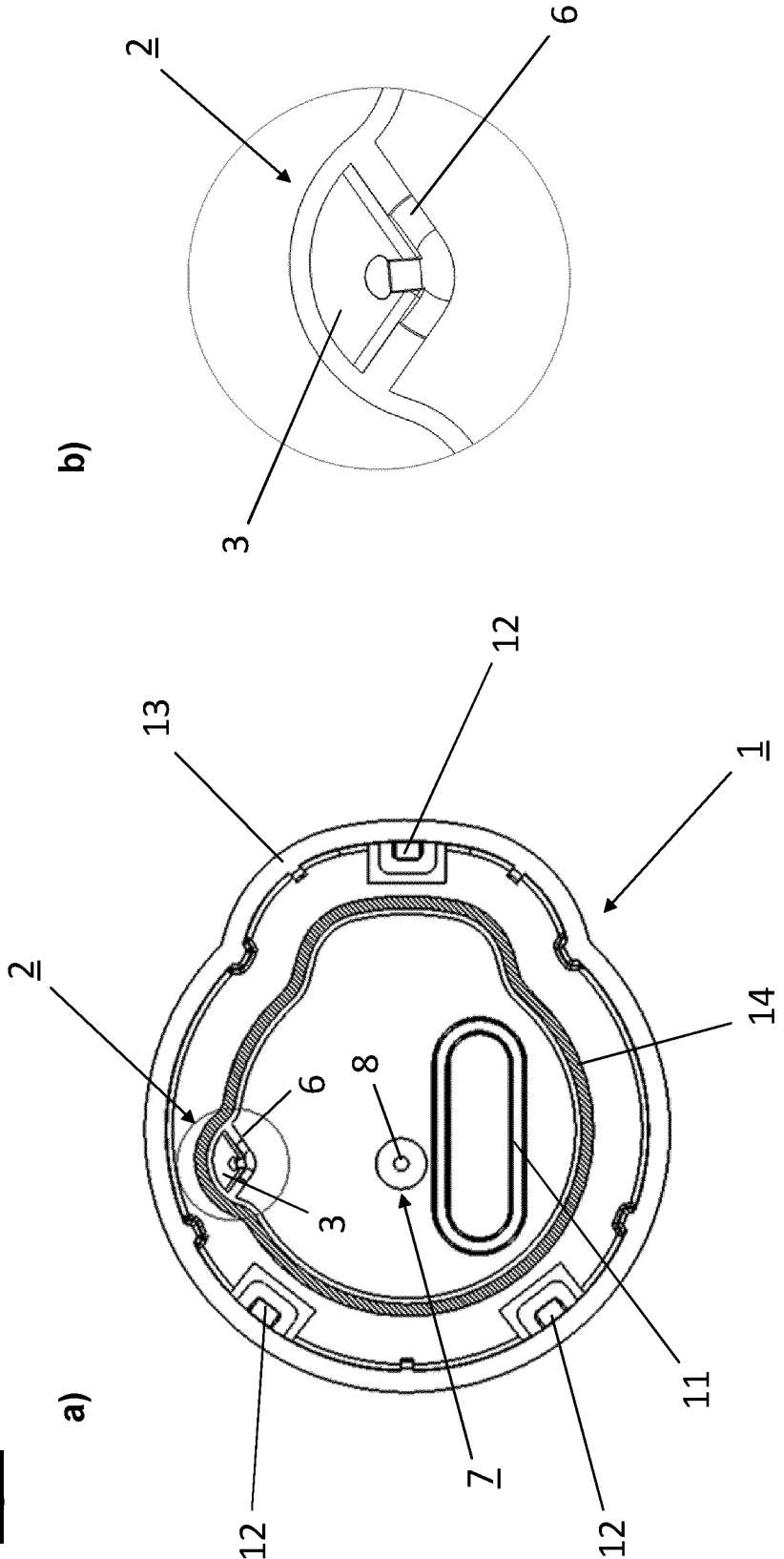
FIG. 2 shows a schematic representation of the rear side of the part (cap) according to FIG. 1.
a) Plan view
b) Enlarged representation of the barrier element

FIGS. 1 and 2 show a part of a device according to the invention, said part being a cap-like element 1 designed to cover the internal space of the device. The cap-like element 1 comprises an inlet port 2 comprising a first opening 3 for introducing a cell suspension into the internal space (see FIGS. 3 to 5) of the device. The inlet port 2 further comprises a tubular channel 4 disposed between the first opening 3 and at least one third opening 5 designed to be connectable to at least one first hose (not shown). The inlet port 2 also comprises a barrier element 6, by which the suspension is deflected in direction of the devices' wall (see FIG. 3) so that the velocity with which the suspension flows is decelerated and the suspension thus flows slowly from the first opening 3 along the wall into the internal space. The barrier element 6 is disposed at the first opening 3 and borders the first opening 3 at a side furthest to the wall. The barrier element 6 is partially arranged between the first opening 3 and the internal space. Accordingly, the barrier element 6 is arranged such that the cell suspension introduced into the internal space gently flows along the inner surface of the wall so that dropping of the suspension from the first opening 3 into the internal space and thus collision of suspension drops with the bottom of the device or the surface of suspension already present therein can be effectively avoided. When a cell suspension is introduced into the inlet port 2, the suspension is deflected by the barrier element 6 in direction of the wall so that its flow is decelerated and the suspension flows slowly from the first opening 3 along the wall into the internal space so that the cells are not exposed to mechanical stress. To keep the distance to be covered by the suspension short, the inlet port 2 and in particular the first opening 3 are disposed in a region near to the devices' wall.

The cap-like element 1 further comprises a venting port 7 comprising a fifth opening 8 for balancing the pressure within the internal space. The venting port 7 further comprises a tubular channel 9 disposed between the fifth opening 8 and at least one sixth opening 10 designed to be connectable to, for example, a filter element in order to avoid contamination of the cell suspension within the internal space.

Figure 6:
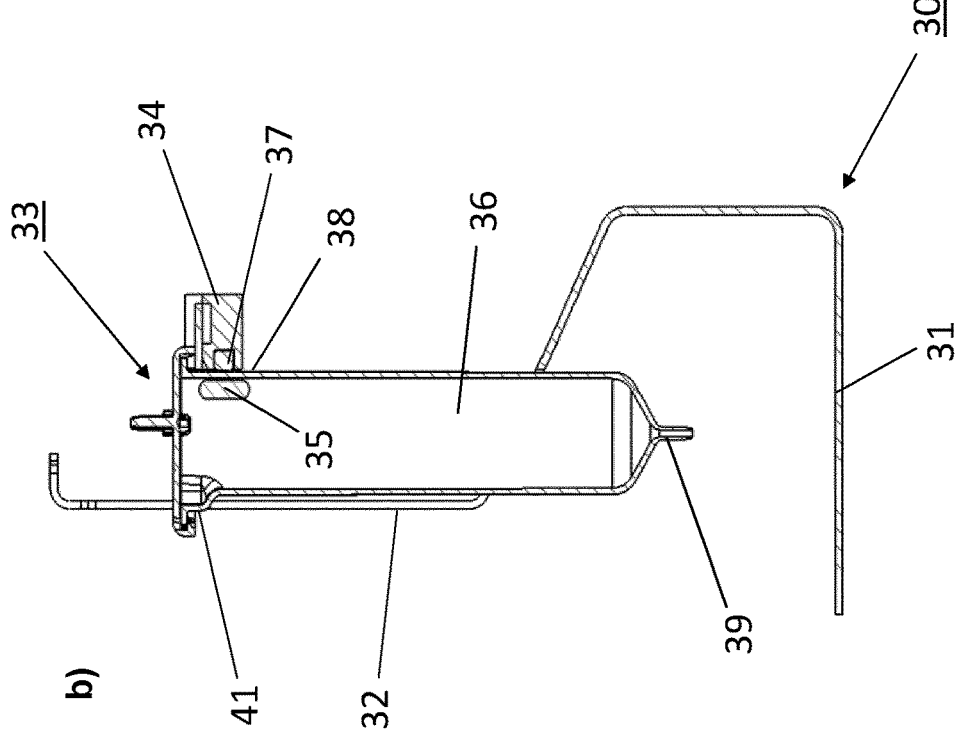
FIG. 6 shows a schematic representation of a preferred embodiment of a support device holding a device according to the invention.
a) Perspective view
b) Longitudinal cut
Figure 6:
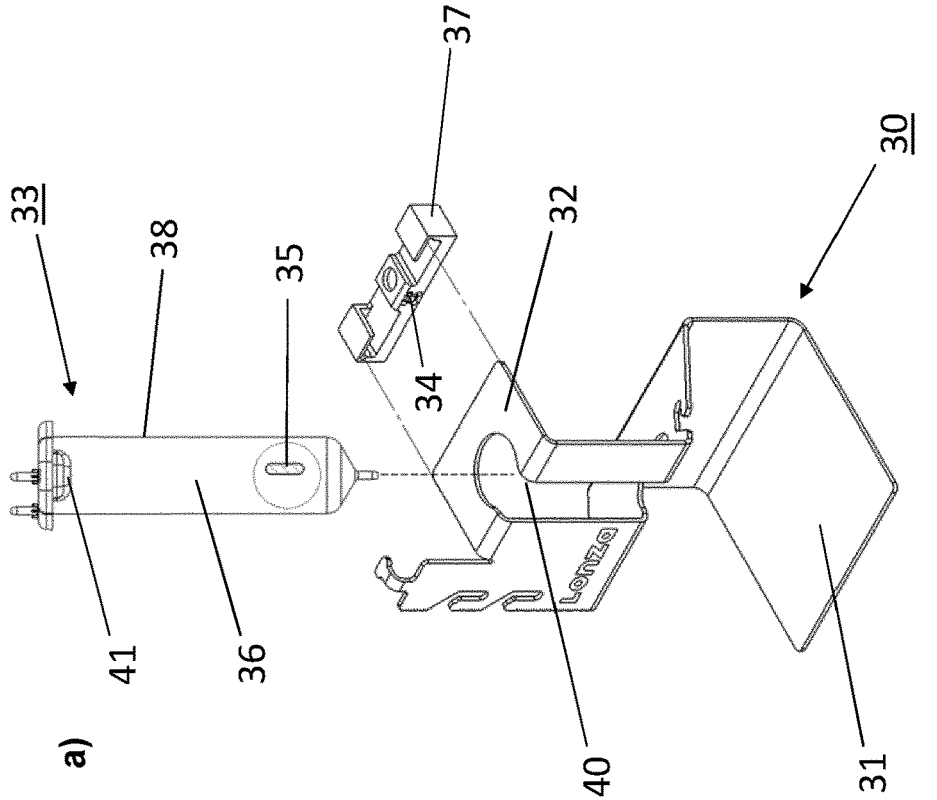

The cap-like element 1 also comprises a protrusion 13 for fixing a position of the device, preferably if the device according to the invention is hold by a support device as shown in FIG. 6. Moreover, at its underside, the cap-like element 1 comprises at least one retainer 11 for holding at least one magnetic element.

The cap-like element 1 can be reversibly attached to the wall surrounding the internal space by snap-action means 12. Additionally, the cap-like element 1 may be irreversibly attached to the wall surrounding the internal space by means of a glued connection. In the latter case, a suitable glue can be applied to glue path 14 before the cap-like element 1 is pressed onto the wall surrounding the internal space.

Figure 3:
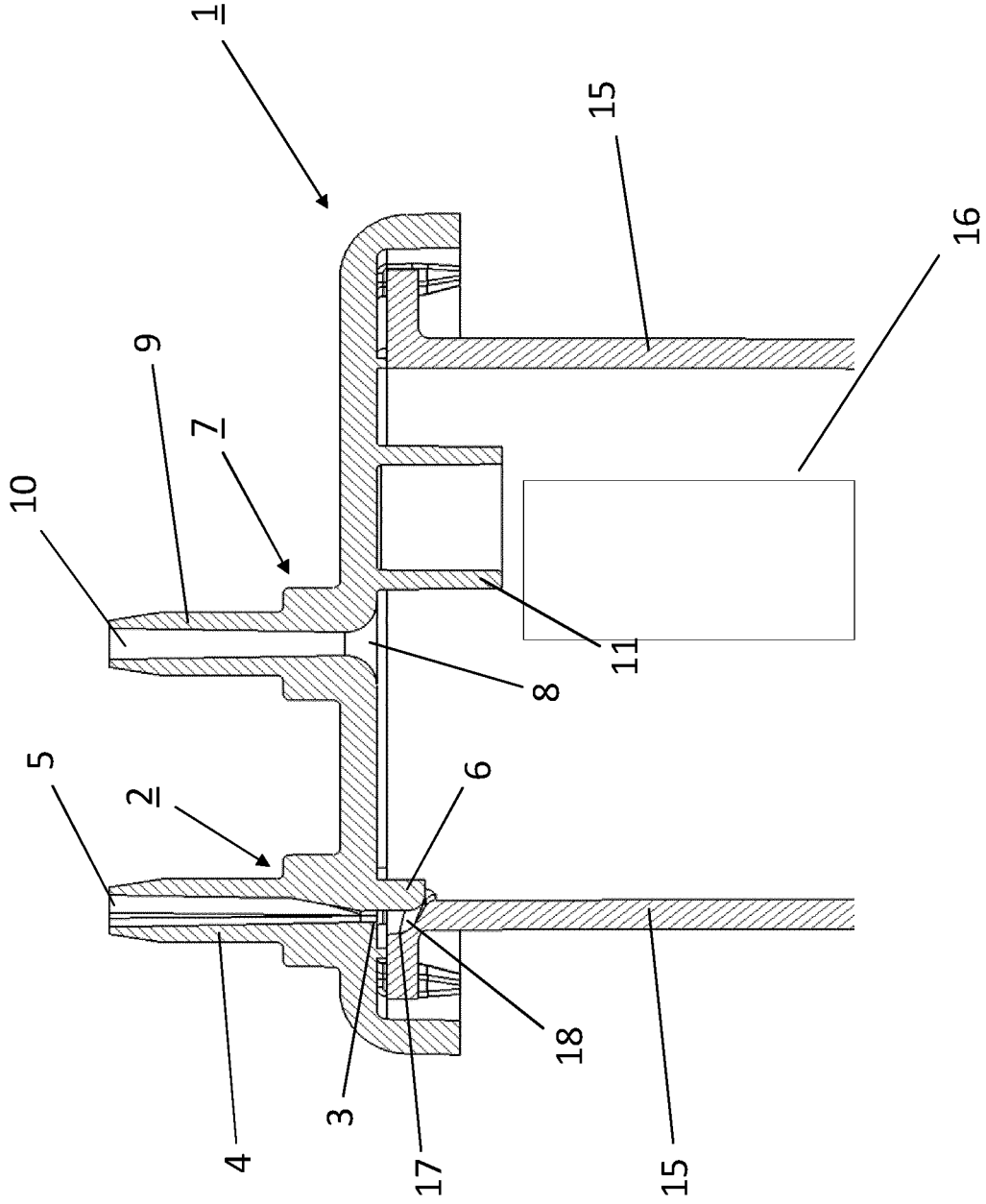
FIG. 3 shows a longitudinal cut through the part (cap) according to FIG. 1 and a part of the wall of a preferred embodiment of a device according to the invention.

FIG. 3 shows a longitudinal cut through the cap-like element 1 according to FIGS. 1 and 2 including a part of the wall 15 of the device according to the invention. As becomes apparent from FIG. 3, the barrier element 6 is arranged such that the suspension is deflected in direction of the wall 15 surrounding the internal space 16 of the device so that it flows along the inner surface of the wall 15 into the internal space 16. To this end, the barrier element 6 is disposed at the first opening 3 and borders the first opening 3 at a side furthest to the wall 15. The barrier element 6 is partially arranged between the first opening 3 and the internal space 16 so as to avoid direct dropping of the suspension into the internal space 16. Accordingly, exposure of the cells to mechanical stress is minimized since collision of suspension drops with the bottom of the device or the surface of suspension already present therein can be avoided. In contrast, if a cell suspension is introduced into the inlet port 2, the suspension is deflected by the barrier element 6 in direction of the wall 15 so that its flow speed is reduced and the suspension can flow slowly from the first opening 3 along the wall 15 into the internal space 16. To keep the distance to be covered by the suspension short, the inlet port 2 and in particular the first opening 3 are disposed in a region near to the wall 15.

The wall 15 comprises a recess 17 which, together with the barrier element 6, forms a cavity 18 emptying into the internal space 16. Thus, the barrier element 6 and the recess 17 are arranged and designed such that the cell suspension introduced into the inlet port 2 is deflected by the barrier element 6 in direction of the recess 17 so that its flow is decelerated. The suspension thus accumulates in the cavity 18 and then flows slowly from the cavity 18 along the wall 15 into the internal space 16. Accordingly, exposure of the cells to mechanical stress can be further reduced. The recess 17 is preferably disposed in a region near to the inlet port 2 and the first opening 3.

The cap-like element 1 further comprises a venting port 7 comprising a fifth opening 8 for balancing the pressure within the internal space. The venting port 7 further comprises a tubular channel 9 disposed between the fifth opening 8 and at least one sixth opening 10 designed to be connectable to, for example, a filter element in order to avoid contamination of the cell suspension within the internal space. Moreover, the cap-like element 1 comprises at its underside at least one retainer 11 for holding at least one magnetic element (e.g., stir bar).

Figure 4:
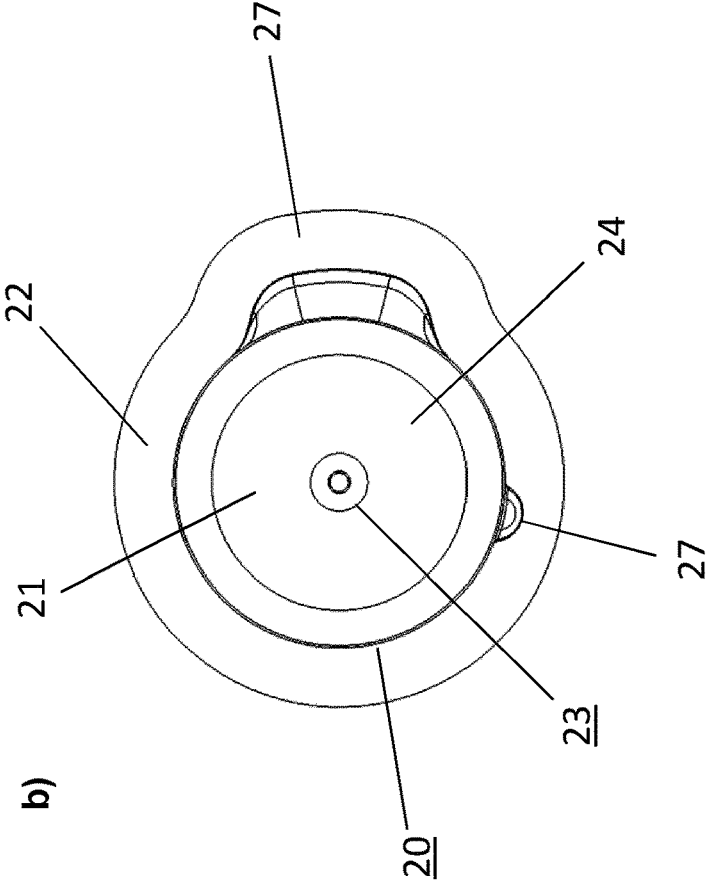
FIG. 4 shows schematic representations of a preferred embodiment of another part (body, wall) of a device according to the invention.
a) Perspective view
b) Top view
Figure 4:
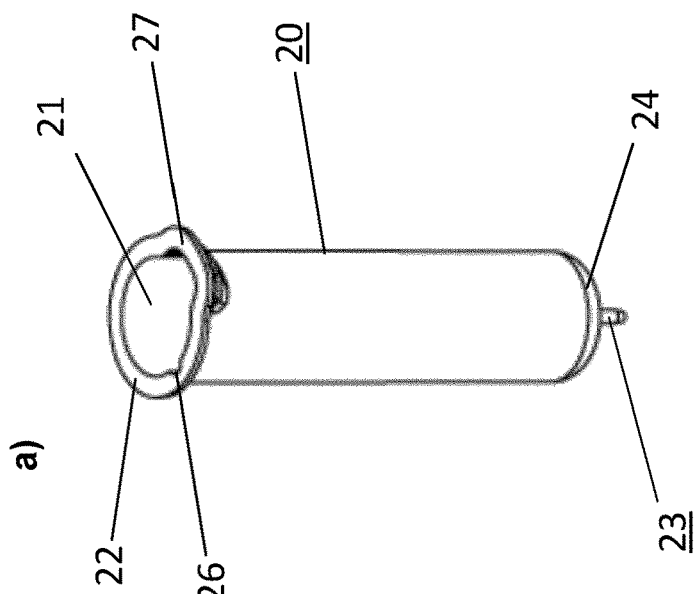
Figure 5:
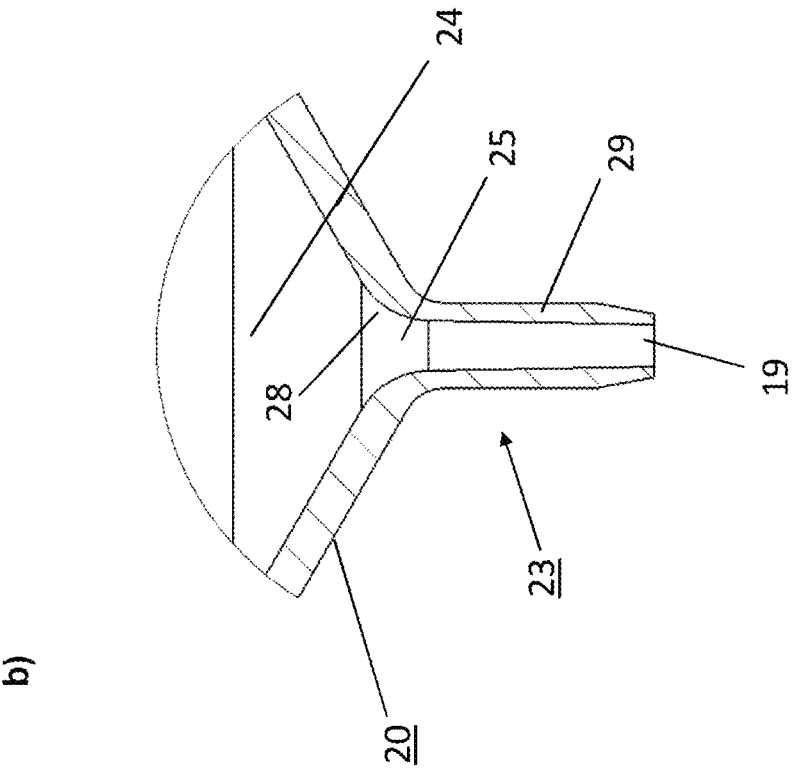
FIG. 5 shows longitudinal cuts through the part (body, wall) according to FIG. 4.
a) Whole part
b) Part bottom (enlarged)
Figure 5:
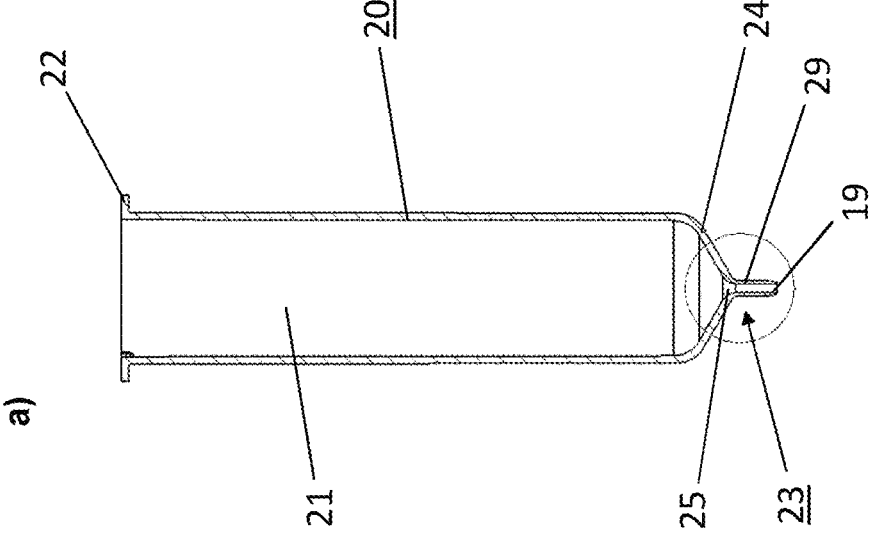

FIGS. 4 and 5 show a part of a device according to the invention, said part being a wall 20 (body) surrounding the internal space 21 of the device according to the invention. The cap-like element 1 shown in FIGS. 1 to 3 may be attached to the upper region 22 of the wall 20 in order to cover the internal space 21. The wall 20 and the internal space 21 both have an elongated form and a vertical orientation, wherein an inlet port (not shown here) and an outlet port 23 are disposed at opposite ends of the internal space 21. The outlet port 23 is disposed at the bottom 24 of the internal space 21 and comprises a second opening 25 for removing the suspension from the internal space 21. The outlet port 23 further comprises a tubular channel 29 disposed between the second opening 25 and a fourth opening 19 designed to be connectable to at least one second hose (not shown).

The wall 20 further comprises a recess 26 which, together with a barrier element (not shown), forms a cavity emptying into the internal space 21. Thus, the barrier element and the recess 26 are arranged and designed such that the cell suspension introduced into the inlet port is deflected by the barrier element in direction of the recess 26 so that its flow is decelerated. The suspension thus accumulates in the cavity and then flows slowly from the cavity along the wall 20 into the internal space 21. Accordingly, exposure of the cells to mechanical stress can be further reduced. The recess 26 is preferably disposed in a region near to the inlet port and the first opening.

Moreover, the wall 20 comprises a protrusion 27 for fixing a position of the device, preferably if the device according to the invention is hold by a support device as shown in FIG. 6.

As becomes apparent from FIG. 5, the outlet port 23 is disposed at a central point at the bottom 24 and the deepest point of the internal space 21, wherein the wall 20 has a steep decline in the bottom area 24. This advantageous configuration allows for residue-free removal of the cell suspension from the internal space 21 so that loss of valuable cells can be minimized. The transition region 28 between the wall 20 and the outlet port 23 is shaped uniformly, i.e. without any unevenness, rims or edges, so that a smooth transition from the internal space 21 to the outlet port 23 is ensured. By this measure, the cell suspension can be removed from the internal space completely, almost without any remaining residues. Moreover, the cells are prevented from unnecessary mechanical stress when they are removed from the internal space 21.

FIG. 6 shows a preferred embodiment of a support device 30 comprising at least one base element 31 and at least one mounting element 32 for holding a device 33 according to the invention. The mounting element 32 comprises a magnetic means 34 for retaining at least one magnetic element 35 contained in the internal space 36 of the device 33. In this embodiment, the magnetic means 34 is a separate member that can be reversibly mounted on the mounting element 32 of the support device 30. The magnetic means 34 is integrated into a plastic member 37 comprising means for attaching it to the mounting element 32. Accordingly, the magnetic means 34 and thus the mounting element 32 serve as a trap for the magnetic element 35, wherein the magnetic element 35 is retained by the magnetic means 34 and fixed at the wall 38 in the top region of the device 33 if the device 33 is fixed to the support device 30 such that it is guided along the magnetic means 34. As a result, the magnetic element 35 is kept away from the outlet port 39 of the device 33 so that it does not impede removal of the cell suspension from the internal space 36 of the device 33.

Moreover, the mounting element 32 comprises a recess 40 for fixing the device 33, said recess 40 corresponding to a protrusion 41 of the wall 38 of the device 33. By this measure, the device 33 can be fixed to the support device 30 in a particular position that is useful for the specific application.

The invention claimed is:

1. Device for providing a cell suspension to an apparatus for treating cells of the suspension, said device comprising
  at least one internal space adapted to hold the cell suspension, wherein said internal space is at least partially surrounded by a wall,
  said device further comprising
  at least one inlet port comprising at least one first opening for introducing the suspension into said internal space and at least one outlet port comprising at least one second opening adapted for removal of the suspension from said internal space, wherein
  the inlet port further comprises at least one barrier element bordering the first opening at a side furthest to the wall and being partially arranged between the first opening and the internal space, wherein the wall comprises at least one recess and the barrier element and the recess form a cavity emptying into the internal space.

2. The device according to claim 1, wherein the first opening of the inlet port opens into the at least one recess of the wall.

3. The device according to claim 1 wherein the inlet port further comprises a tubular channel disposed between the first opening and at least one third opening designed to be connectable to at least one first hose.

4. The device according to claim 3, wherein the outlet port further comprises a tubular channel disposed between the second opening and at least one fourth opening designed to be connectable to at least one second hose.

5. The device according to claim 4, further comprising at least one venting port comprising at least one fifth opening adapted for balancing pressure within the internal space.

6. The device according to claim 3, wherein the inlet port is part of a cap-like element designed to cover the internal space.

7. The device according to claim 6, wherein the cap-like element further comprises at least one retainer adapted to hold at least one magnetic element.

8. The device according to claim 3, wherein the outlet port is disposed at a central point at the bottom of the internal space.

9. The device according to claim 1, wherein the inlet port is part of a cap-like element designed to cover the internal space.

10. The device according to claim 9, wherein the cap-like element further comprises at least one retainer adapted to hold at least one magnetic element.

11. The device according to claim 9, wherein the outer surface of the wall and/or the cap-like element comprises at least one recess and/or protrusion for fixing a position of the device.

12. The device according to claim 9, wherein the cap-like element further comprises at least one venting port comprising at least one fifth opening adapted for balancing pressure within the internal space.

13. The device according to claim 1, wherein a transition region between the wall and the outlet port is shaped uniformly.

14. The device according to claim 1, wherein the outlet port is disposed at a central point at a bottom of the internal space.

15. The device according to claim 1, wherein the internal space has a deepest point and the outlet port is disposed at the deepest point.

16. The device according to claim 1, wherein a bottom of the internal space comprises a bottom area comprising a flat and circular region for receiving and guiding a magnetic element.

17. The device according to claim 1, further comprising at least one venting port comprising at least one opening adapted for balancing pressure within the internal space.

\* \* \* \* \*